United States Patent [19]

Meyer et al.

[11] Patent Number: 4,952,726
[45] Date of Patent: Aug. 28, 1990

[54] PHENYLSULFONYL ISOCYANATES AND THIOISOCYANATES

[75] Inventors: Willy Meyer, Riehen; Konrad Oertle, Therwil, both of Switzerland

[73] Assignee: Ciba-Geigy Corporation, Ardsley, N.Y.

[21] Appl. No.: 440,004

[22] Filed: Nov. 21, 1989

Related U.S. Application Data

[60] Division of Ser. No. 179,339, Apr. 8, 1988, Pat. No. 4,908,467, which is a division of Ser. No. 30,529, Mar. 27, 1987, Pat. No. 4,759,793, which is a division of Ser. No. 810,010, Dec. 17, 1985, Pat. No. 4,671,819, which is a continuation of Ser. No. 717,639, Mar. 29, 1985, abandoned, which is a continuation-in-part of Ser. No. 590,928, Mar. 19, 1984, abandoned.

[30] Foreign Application Priority Data

Mar. 28, 1983 [CH] Switzerland ........................ 1677/83
Aug. 11, 1983 [CH] Switzerland ........................ 4393/83

[51] Int. Cl.$^5$ .................. C07C 303/00; C07C 255/00; C07C 307/00; C07C 143/00
[52] U.S. Cl. ...................................... 562/870; 564/42; 564/43; 560/12; 558/413
[58] Field of Search .................. 558/61, 413; 562/870; 564/42, 43; 560/12

[56] References Cited

U.S. PATENT DOCUMENTS 3,420,882 1/1969 Muth et al. ........................ 564/43
4,826,528 5/1989 Mengel et al. ........................ 71/92

*Primary Examiner*—John M. Ford
*Assistant Examiner*—Robert C. Whittenbaugh
*Attorney, Agent, or Firm*—Kevin T. Mansfield; Edward McC. Roberts

[57] ABSTRACT

N-Phenylsulfonyl-N'-pyrimidinyl- and -triazinylureas of the formula I

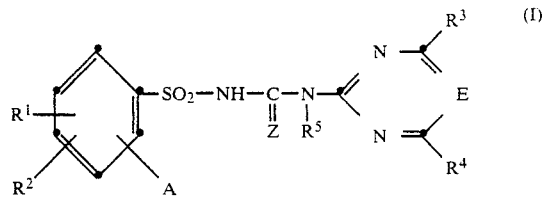

wherein

A is 3,3,3-trifluoropropyl or 3,3-difluorobutyl,
$R^1$ is hydrogen, halogen, nitro, cyano, $C_1$–$C_4$-alkyl, $C_1$–$C_4$-haloalkyl, $C_1$–$C_4$-alkoxy, $C_1$–$C_4$-alkylthio, $C_1$–$C_4$-alkylsulfinyl, $C_1$–$C_4$-alkylsulfonyl, —CO—$R^6$, —$NR^7R^8$, —CO—$NR^9R^{10}$ or —$SO_2$—$NR^{11}R^{12}$,
$R^2$ is hydrogen, halogen, $C_1$–$C_4$-alkyl, $C_1$–$C_4$-alkoxy, $C_1$–$C_4$-alkylthio, $C_1$–$C_4$-alkysulfinyl or $C_1$–$C_4$-alkylsulfonyl,
$R^3$ and $R^4$ independently of one another are each hydrogen, halogen, $C_1$–$C_4$-alkyl, $C_1$–$C_4$-haloalkyl, $C_2$–$C_4$-haloalkoxy, $C_1$–$C_4$-alkylthio, $C_1$–$C_4$-haloalkylthio, $C_2$–$C_4$-alkoxyalkyl, $C_1$–$C_4$-alkoxy or —$NR^{13}R^{13}$,
$R^5$ is hydrogen, $C_1$–$C_4$-alkyl or $C_1$–$C_4$-alkoxy,
$R^6$ is $C_1$–$C_4$-alkoxy, $C_1$–$C_4$-haloalkoxy, $C_1$–$C_4$-alkylthio, $C_2$–$C_6$-alkoxyalkoxy, hydrogen, $C_1$–$C_4$-alkyl or $C_1$–$C_4$-haloalkyl,
$R^7$, $R^8$, $R^9$, $R^{10}$, $R^{11}$, $R^{12}$ and $R^{13}$ independently of one another are each hydrogen or $C_1$–$C_4$-alkyl,
E is nitrogen or the methine bridge, and
Z is oxygen or sulfur;

and also the salts of these compounds.

2 Claims, No Drawings

PHENYLSULFONYL ISOCYANATES AND THIOISOCYANATES

CROSS REFERENCE TO RELATED APPLICATION

This is a divisional of application Ser. No. 179,339 filed on Apr. 8, 1988, now U.S. Pat. No. 4,908,467 which in turn is a divisional of Ser. No. 030,529 filed on Mar. 27, 1987, now U.S. Pat. No. 4,759,793 which in turn is a divisional of Ser. No. 810,010 filed Dec. 17, 1985 now U.S. Pat. No. 4,671,819 which in turn is a continuation of Ser. No. 717,639 filed Mar. 29, 1985 now abandoned which in turn is a continuation-in-part of Ser. No. 590,928 filed Mar. 19, 1984 now abandoned.

The present invention relates to novel N-phenylsulfonyl-N'-pyrimidinyl- and -triazinylureas which have a herbicidal action and an action regulating plant growth, to processes for producing them, to compositions containing them as active ingredients, and to the use thereof for controlling weeds, particularly selectively in cultivated crops, or for regulating and reducing plant growth.

The N-phenylsulfonyl-N'-pyrimidinyl- and -triazinylureas according to the invention correspond to the general formula

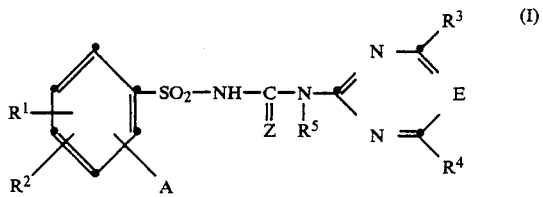

wherein
A is 3,3,3-trifluoropropyl or 3,3-difluorobutyl,
$R^1$1 is hydrogen, halogen, nitro, cyano, $C_1$–$C_4$-alkyl, $C_1$–$C_4$-haloalkyl, $C_1$–$C_4$-alkoxy, $C_1$–$C_4$-alkylthio, $C_1$–$C_4$-alkylsulfinyl, $C_1$–$C_4$-alkylsulfonyl, -CO-$R^6$, -$NR^7R^8$, -CO-$NR^9R^{10}$ or -$SO_2$-$NR^{11}R^{12}$,
$R^2$ is hydrogen, halogen, $C_1$–$C_4$-alkyl, $C_1$–$C_4$-alkoxy, $C_1$–$C_4$-alkylthio, $C_1$–$C_4$-alkylsulfinyl or $C_1$–$C_4$-alkylsulfonyl,
$R^3$ and $R^4$ independently of one another are each hydrogen, halogen, $C_1$–$C_4$-alkyl, $C_1$–$C_4$-haloalkyl, $C_2$–$C_4$-haloalkoxy, $C_1$–$C_4$-alkylthio, $C_1$–$C_4$-haloalkylthio, $C_2$–$C_4$-alkoxyalkyl, $C_1$–$C_4$-alkoxy or -$NR^{12}R^{13}$,
$R^5$ is hydrogen, $C_1$–$C_4$-alkyl or $C_1$–$C_4$-alkoxy, $R^6$ is $C_1$–$C_4$-alkoxy, $C_1$–$C_4$-haloalkoxy, $C_1$–$C_4$-alkylthio, $C_2$–$C_6$-alkoxyalkoxy, hydrogen, $C_1$–$C_4$-alkyl or $C_1$–$C_4$-haloalkyl,
$R^7$, $R^8$, $R^9$, $R^{10}$, $R^{11}$, $R^{12}$ and $R^{13}$ independently of one another are each hydrogen or $C_1$–$C_4$-alkyl,
E is nitrogen or the methine bridge, and
Z is oxygen or sulfur;
and the invention relates also to the salts of these compounds.

Urea compounds, triazine compounds and pyrimidine compounds having herbicidal activity are known in general Sulfonylurea compounds having a herbicidal action and an action regulating plant growth have recently been described, for example, in the European Patent Publications Nos. 44210, 44807, 44808 and 44809.

By alkyl in the definitions is meant straight-chain or branched-chain alkyl, for example: methyl, ethyl, n-propyl, i-propyl, the four isomeric butyl groups, n-amyl, i-amyl, 2-amyl, 3-amyl, n-hexyl or i-hexyl. Methyl and ethyl are preferred.

And by alkoxy is meant: methoxy, ethoxy, n-propyloxy, i-propyloxy and the four isomeric butyloxy groups, in particular however methoxy, ethoxy or i-propoxy.

Examples of alkylthio are: methylthio, ethylthio, n-propylthio, i-propylthio and n-butylthio, especially methylthio and ethylthio.

Examples of alkylsulfinyl are: methylsulfinyl, ethylsulfinyl, n-propylsulfinyl and n-butylsulfinyl, in particular methylsulfinyl and ethylsulfinyl.

Examples of alkylsulfonyl are: methylsulfonyl, ethylsulfonyl, n-propylsulfonyl and n-butylsulfonyl, especially methylsulfonyl and ethylsulfonyl.

Halogen in the definitions, as well as in haloalkyl, haloalkoxy, haloalkylsulfinyl, haloalkylsulfonyl and haloalkylthio, is fluorine, chlorine and bromine, preferably however fluorine and chlorine.

By haloalkyl or haloalkyl moieties of the above-defined substituents $R^1$ to $R^{13}$ are accordingly meant for example: chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl or 1,1,2,3,3,3-hexafluoropropyl, particularly fluoromethyl, chloromethyl, difluoromethyl and trifluoromethyl.

The invention embraces likewise the salts which the compounds of the formula I form with amines, alkali metal and alkaline-earth metal bases or quaternary ammonium bases.

To be emphasised among alkali metal and alkaline-earth metal hydroxides as salt formers are the hydroxides of lithium, sodium, potassium, magnesium or calcium, in particular those of sodium and potassium.

Examples of amines suitable for forming salts are: primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and i-quinoline, especially ethyl-, propyl-, diethyl- or triethylamine, but particularly isopropylamine and diethanolamine.

Examples of quaternary ammonium bases are in general the cations of haloammonium salts, for example the tetramethylammonium cation, the trimethylbenzylammonium cation, the triethylbenzylammonium cation, the tetraethylammonium cation or the trimethylethylammonium cation, but also the ammonium cation.

Preferred compounds of the formula I according to the invention are those in which
(a) $R^1$ is hydrogen; or
(b) $R^2$ is hydrogen; or
(c) Z is oxygen; or
(d) $R^5$ is hydrogen; or
(e) $R^3$ and $R^4$ together contain at most 4 carbon atoms;
(f) the radical A occupies the 2-position on the phenyl nucleus.

Further preferred groups of active substances are characterised in that in the compounds of the formula I $R^1$, $R^2$ and $R^5$ are hydrogen and Z is oxygen, or that $R^3$ and $R^4$ together contain at most 4 carbon atoms, and the radical A occupies the 2-position of the phenyl ring and contains at least one fluorine atom.

A group of active substances to be particularly emphasised contains compounds of the formula I in which $R^1$, $R^2$ and $R^5$ are hydrogen and Z is oxygen, $R^3$ and $R^4$ together contain at most 4 carbon atoms, and the radical A occupies the 2-position of the phenyl ring.

The following are mentioned as preferred individual compounds:

N-[2-(3,3,3-trifluoropropyl)-phenylsulfonyl]-N'-(4,6-dimethoxy-pyrimidin-2-yl)-urea, N-[2-(3,3,3-trifluoropropyl)-phenylsulfonyl]-N'-(4,6-dimethoxy-1,3,5-triazin-2-yl)-urea, N-[2-(3,3-difluorobutyl)-phenylsulfonyl]-N'-4-methoxy-6-methyl-1,3,5-triazin-2-yl)-urea, and N-[2-(3,3,3-trifluoropropyl)-phenylsulfonyl]-N'-(4-methoxy-6-methyl-1,3,5-triazin-2-yl)-urea.

The compounds of the formula I are produced in an inert organic solvent.

One process for obtaining the compounds of the formula I comprises reacting a phenylsulfonamide of the formula II

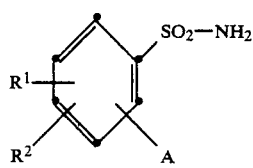

wherein A, $R^1$ and $R^2$ have the meanings defined under the formula I, in the presence of a base, with an N-pyrimidinyl-or -triazinylcarbamate of the formula III

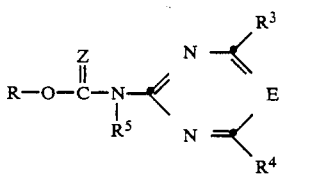

wherein E, $R^3$, $R^4$, $R^5$ and Z have the meanings defined under the formula I, and R is Phenyl, alkyl or substituted phenyl.

Compounds of the formula I are produced, using a second process, by reacting a phenylsulfonylisocyanate or -isothiocyanate of the formula IV

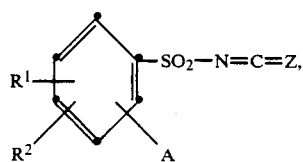

wherein A, $R^1$, $R^2$ and Z have the meanings defined under the formula I, optionally in the presence of a base, with an amine of the formula V

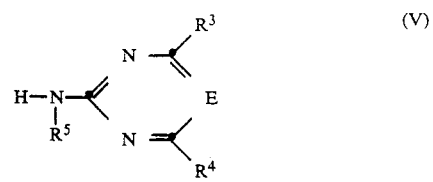

wherein E, $R^3$, $R^4$ and $R^5$ have the meanings defined under the formula I.

There are produced, using a further process, the compounds of the formula I in which $R^5$ is hydrogen by reacting a sulfonamide of the formula II given above, optionally in the presence of a base, with an isocyanate or isothiocyanate of the formula VI

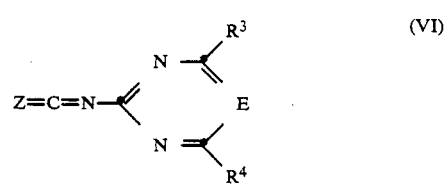

wherein E, $R^3$, $R^4$, $R^5$ and Z have the meanings defined under the formula I.

Furthermore, the compounds of the formula I can be obtained also by reacting an N-phenylsulfonylcarbamate of the formula VII

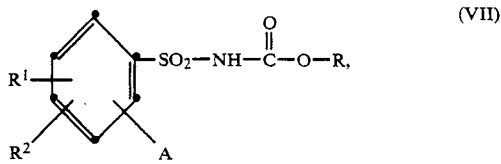

wherein A, $R^1$ and $R^2$ have the meanings defined under the formula I, and R is phenyl, alkyl or substituted phenyl, with an amine of the formula V given above.

In addition, the compounds of the formula I are produced by hydrogenating to saturation a sulfonylurea of the formula VIII

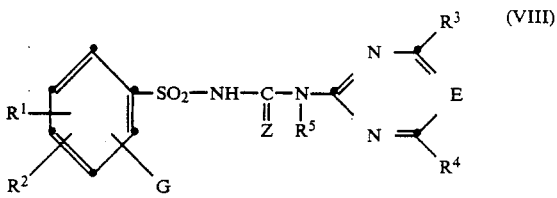

wherein $R^1$, $R^2$, $R^3$, $R^4$, $R^5$, E and Z have the meanings defined under the formula I, and G is 3,3,3-trifluoro-1-propenyl or 3,3-difluoro-1-butenyl radical.

The resulting ureas of the formula I can if desired be converted, by means of amines, alkali metal hydroxides or alkaline-earth metal hydroxides or quaternary ammonium bases, into addition salts. This is effected for example by reaction with the equivalent amount of a base, and removal of the solvent by evaporation.

The reactions to give compounds of the formula I are performed advantageously in aprotic, inert organic solvents. Such solvents are: hydrocarbons, such as benzene, toluene, xylene or cyclohexane, chlorinated hydrocarbons, such as methylene chloride, chloroform, carbon tetrachloride or chlorobenzene, ethers, such as diethyl ether, ethylene glycol dimethyl ether, diethylene glycol dimethyl ether, tetrahydrofuran or dioxane, nitriles, such as acetonitrile or propionitrile, amides, such as dimethylformamide, diethylformamide or N-methylpyrrolidinone. The reaction temperatures are preferably between −20° and +120° C. The reactions of the coupling processes proceed in general slightly exothermically, and can be performed at room temperature. For the purpose of shortening the reaction time or for initiating the reaction, it is advantageous to apply heat for a short time up to the boiling point of the reaction mixture The reaction times can be shortened also by the addition of a few drops of a base or of isocyanate as a reaction catalyst. Suitable as bases are in particular tertiary amines, such as trimethylamine, triethylamine, quinuclidine, 1,4-diazabicyclo-(2,2,2)-octane, 1,5-diazabicyclo(4,3,0)non-5-ene or 1,5-diazabicyclo(5,4,0)-undec-7-ene.

The halogenation processes are performed at reaction mixture temperatures of between 0 ° and 100° C. A procedure which has proved to be in this respect particularly advantageous is the irradiation of the reaction solution with light, or the addition of a radical chain reaction starter, such as dibenzoyl peroxide or α,α'-azoisobutyronitrile, and the use of a chlorinated hydrocarbon, such as methylene chloride, chloroform or carbon tetrachloride, as solvent. The hydrogenating process is generally performed in an inert solvent, such as carboxylic acids, alcohols, esters or hydrocarbons, in a hydrogen atmosphere and in the presence of a hydrogenating catalyst such as Raney nickel, or palladium or platinum catalysts.

The final products of the formula I can be isolated by concentration by evaporation and/or by removal of the solvent by evaporation, and purified by recrystallisation or trituration of the solid residue in solvents in which the products do not readily dissolve, such as ethers, aromatic hydrocarbons or chlorinated hydrocarbons.

The starting materials III, V and VI are known from the literature and can be produced by known methods. In particular, compounds of the formulae III and VI can be obtained by known methods from the compounds of the formula V.

The starting materials of the formula VIII and processes for producing them are described in the European Patent Application No. 102925.

The intermediates of the formulae II, IV and VII are novel and were developed specially for the synthesis of the compounds of the formula I. They form therefore a part of the subject matter of the present invention.

The novel intermediates of the formula II can be obtained by various methods. They can be obtained for example by diazotising anilines of the formula X

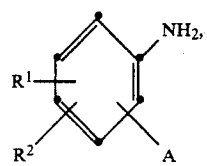

(X)

wherein $R^1$, $R^2$ and A have the meanings defined under the formula I, and exchanging the diazo group with sulfur dioxide in the presence of a catalyst, such as copper(I) chloride, in hydrochloric acid or acetic acid, and reacting the formed phenylsulfonyl chloride with ammonium hydroxide solution.

The compounds of the formula II can likewise be obtained by converting a phenylsulfonic acid of the formula XI

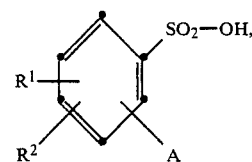

(XI)

wherein $R^1$, $R^2$ and A have the meanings defined under the formula I, by treatment with a chlorinating agent, such as $PCl_5$, $POCl_3$, $COCl_2$ or $SOCl_2$, into the corresponding phenylsulfonyl chloride, and reacting this with ammonium hydroxide solution.

The compounds of the formula II can also be obtained by converting a benzylthio ether of the formula XII

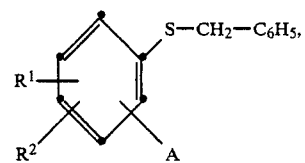

(XII)

wherein $R^1$, $R^2$ and A have the meanings defined under the formula I, by treatment with chlorine into the corresponding phenylsulfonyl chloride, and reacting this with ammonium hydroxide solution.

The compounds of the formula II in which A is $C_2$–$C_6$-haloalkyl can also be produced by hydrogenating or halogenating to saturation a phenylsulfonamide of the formula XIII

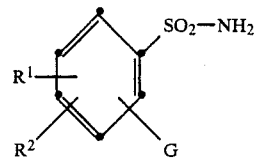

(XIII)

wherein $R^1$, $R^2$ and G have the meanings defined under the formula VIII.

The likewise novel phenylsulfonylisocyanates of the formula IV can be obtained for example by reaction of the sulfonamides of the formula II with phosgene in the presence of butylisocyanate, in a chlorinated hydrocarbon as solvent, at the reflux temperature. Similar methods of preparation are described in "Neuere Methoden der preparativen organischen Chemie", Vol VI, 211–229, Verlag Chemie, Weinheim, 1970.

The isothiocyanates of the formula IV are obtained by treatment of the sulfonamides of the formula II with carbon disulfide and potassium hydroxide, and subsequent reaction of the dipotassium salt with phosgene. Such processes are described in Arch. Pharm. 299, 174 (1966).

The N-phenylsulfonylcarbamates of the formula VII are obtained by reaction of the sulfonamides of the formula II with diphenyl carbonate in the presence of a base. Similar processes are mentioned in the Japanese Patent Specification No. 61 169.

The starting materials of the formulae X, XI and XII are in general known and can be produced by known processes.

The compounds of the formula XIII are described in the European Patent Application No. 102925.

The processes for producing the intermediates proceed generally under conditions which are the same as those given for the processes for the production of the final products.

The active substances of the formula I are stable compounds, and the handling of them necessitates no special precautions being taken.

In smaller applied amounts, the compounds of the formula I are characterised by good selective growth-inhibiting and selective herbicidal properties, which render the compounds excellently suitable for use in crops of useful plants, especially in crops of sugar cane, cereals, cotton, soya-bean, maize and rice. Also destroyed in some cases are weeds which hitherto could be dealt with only by the application of total herbicides.

The mode of action of these active substances is unusual. Many are capable of being translocated, that is to say, they are taken up by the plant and transported to other locations, where they produce the desired effect. It is thus possible for example by surface treatment of perennial weeds to destroy them at the roots. The novel compounds of the formula I are effective in applied amounts which are very small compared with the amounts required to obtain the same effect using other herbicides and plant-growth regulators.

The compounds of the formula 1 also have excellent properties for regulating plant growth, the effects of which can mean an increase in the yield of cultivated plants or of harvested crops. Many compounds of the formula I also exhibit an action reducing plant growth to an extent dependent on the concentration. Both monocotyledons and dicotyledons are impaired in their growth.

Thus, for example, the leguminosae frequently planted as cover crops in agriculture in tropical regions can be selectively inhibited in their growth by the compounds of the formula I, the result being that soil erosion between the cultivated plants is prevented, without the cover crops being able to compete with the main cultivated crop.

A reduction of the vegetative growth enables in the case of many cultivated plants the crop density to be increased, so that higher yields for the same area of land can be achieved.

An additional factor contributing to the increase in yield with the use of growth inhibitors is that the formation of blossom and fruit benefits to a greater extent from the nutritive substances, because the vegetative growth is restricted.

In the case of monocotyledonous plants, for example grasses, or cultivated plants such as cereals, a reduction of vegetative growth is sometimes desirable and advantageous. A reduction of growth of this kind is of economic interest with regard to, amongst other things, grasses, for as a consequence it is possible to reduce the frequency of the cutting of grass in ornamental gardens, Parks and sports grounds, or along the verges of highways. Of importance also is the inhibition of the growth of herbaceous and ligneous plants at the edges of roads and in the vicinity of overhead transmission lines, or quite generally in areas where a strong growth is undesirable.

Also important is the application of growth regulators for reducing the growth in height of cereals, since a shortening of the stems lessens or completely removes the danger of the snapping off (flattening) of the plants before harvesting. Furthermore, growth regulators can result in a strengthening of the stems of cereal crops, a further factor acting to prevent bending of the stems of the plants.

The compounds of the formula I are likewise suitable for preventing the sprouting of stored potatoes. Shoots frequently form on potatoes being stored during the winter, and these shoots cause shrinkage, loss in weight and rotting.

With larger applied amounts of active substance, all the tested plants are impaired in their development to the extent that they wither.

The present invention relates also to herbicidal and plant-growth-regulating compositions containing a novel active ingredient of the formula I, and also to Processes for the pre- and post-emergence controlling of weeds, and for the reduction of growth of monocotyledonous and dicotyledonous plants, particularly that of grasses, tropical cover crops and side shoots of tobacco plants.

The compounds of the formula I are used either in an unmodified form or preferably in compositions, together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objects to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl-or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical Properties, it is also possible to add highly dispersed silicic acid or highly dispersed absorbent polymers. Suitable granulated adsorptive carriers are porous types for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding Phosphates, for example salts of the phosphoric ester of a P-nonylphenol-(4–14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:

"McCutcheon's Detergents and Emulsifiers Annual" MC Publishing Corp., Ridgewood, N.J., 1981; H. Stache, "Tensid-Taschenbuch" (Tenside Handbook), 2nd Edition, C. Hanser Verlag, Munich, Vienna, 1981; M. and J. Ash, "Encyclopedia of Surfactants", Vol.I–III, Chemical Publishing Co., New York, 1980–1981.

The agrochemical preparations contain as a rule 0.1 to 95%, especially 0.1 to 80%, of active ingredient of the formula I, 1 to 99% of a solid or liquid additive, and 0 to 25%, particularly 0.1 to 25%, of a tenside.

Preferred formulations are made up in particular as follows (%=percent by weight):

Emulsifiable concentrates active ingredient: 1 to 20%, preferably 5 to 10%
surface active agent: 5 to 30%, preferably 10 to 20%
liquid carrier: 50 to 94%, preferably 70 to 85%.

Dusts active ingredient: 0.1 to 10%, preferably 0.1 to 1%
solid carrier: 99.9 to 90% preferably 99.9 to 99%.

Suspension concentrates active ingredient: 5 to 75%, preferably 8 to 50%
water: 94 to 25%, preferably 90 to 30%
surface-active agent: 1 to 40%, preferably 2 to 30%.

Wettable powders active ingredient: 0.5 to 90%, preferably 1 to 80%
surface-active agent: 0.5 to 20%, preferably 1 to 15%
solid carrier: 5 to 95%, preferably 15 to 90%.

Granulates active ingredient: 0.5 to 30%, preferably 3 to 15%
solid carrier: 99.5 to 70%, preferably 97 to 85%.

Whereas commercial products are preferably in the form of concentrated compositions, the compositions employed by the end-user are as a rule diluted. The preparations can for application be diluted down to 0.001% of active ingredient. The applied amounts are usually 0.001 to 10 kg, preferably 0.025 to 5, kg of active substance per hectare.

The compositions can also contain additives such as stabilisers, antifoaming agents, viscosity regulators, binders and adhesives, as well as fertilisers or other active substances for obtaining special effects.

In the following Examples, the temperatures are given in degrees Centigrade (°C.), and pressures in millibars (mb).

Production Examples

Example H1

N-[2-(3,3,3-Trifluoropropyl)-phenylsulfonyl]-N'-(4,6-dimethoxy-1,3,5-triazin-2-yl)-urea (a) 2-(3,3,3-Trifluoropropyl)-phenylsulfonamide A mixture of 50.2 g of 2-(3,3,3-trifluoro-1-propenyl)-phenylsulfonamide, 500 ml of ethyl acetate and 5 g of a 5% Pd/C catalyst is shaken for ½ hour at 20°–25° C. in a hydrogen atmosphere The catalyst is then filtered off, the mixture is concentrated by evaporation, and the residue is crystallised from a mixture of methylene chloride and ether to thus yield 49.6 g of 2-(3,3,3-trifluoropropyl)phenylsulfonamide, m.p. 148°-149° C.

(b)
N-[2-(3,3,3-Trifluoropropyl)-phenylsulfonyl]-N'-methyl urea 11.4 g of methylisocyanate are added to a suspension of 40.5 g of 2-(3,3,3-trifluoro)-phenylsulfonamide in 250 ml of absolute methylene chloride, and there are subsequently added dropwise at 20°-25° C., within 15 minutes, 20.2 g of triethylamine. The clear solution which forms is stirred at 20°-25° C. for one hour and is then completely concentrated by evaporation; the residue is afterwards dissolved in a 5% sodium carbonate solution and acidified with 10% hydrochloric acid to thus obtain 46.3 g of N-[2-(3,3,3-trifluoropropyl)-phenylsulfonyl]-N'-methylurea, m.p. 176°-177° C.

(c) 2-(3,3,3-Trifluoropropyl)-phenylsulfonylisocyanate 40.3 g of N-[2-(3,3,3-trifluoropropyl)-phenylsulfonyl]- N'-methylurea are suspended in 700 ml of chlorobenzene, and dried by the azeotropic distilling off of about 150 ml of solvent. There are then introduced at 120°-130° C. 71 g of phosgene in the course of 90 minutes. The yield after complete concentration of the formed solution by evaporation is 37.3 g of 2-(3,3,3-trifluoropropyl)-phenylsulfonylisocyanate in the form of yellowish oil, which can be directly further reacted.

(d)
N-[2-(3,3,3-Trifluoropropyl)-phenylsulfonyl]-N'(4,6-dimethoxy-1,3,5-triazin-2-yl)-urea 5.6 g of 2-(3,3,3-trifluoropropyl)-phenylsulfonylisocyanate and 3.12 g of 2-amino-4,6-dimethoxy-1,3,5-triazine are stirred up in 60 ml of absolute dioxane at 70°-80° C. for 2 hours. The mixture is subsequently treated with active charcoal, filtered, and concentrated by evaporation to about 1/5 of the volume. There crystallise from the residue, after the addition of ether, 6.8 g of N-[2-(3,3,3-trifluoropropyl)-phenylsulfonyl]-N'-(4,6-dimethoxy-1,3,5-triazin-2-yl)-urea, m.p. 177°-178° C.

Example H2

N-[2-(3,3,3-Trifluoropropyl)-phenylsulfonyl]-N'-(4-dimethylamino-6-methoxy-pyrimidin-2-yl)-urea (a)
N-[2-(3,3,3-Trifluoropropyl)-phenyl]-phenylcarbamate 2.8 g of 2-(3,3,3-trifluoropropyl)-phenylsulfonamide in 25 ml of dimethylformamide are added dropwise at a temperature of 15°-20° C., within 5 minutes, to a suspension of 0.5 g of 55% sodium hydride in 10 ml of absolute dimethylformamide, and the suspension is stirred for 10 minutes before the dropwise addition of 2.5 g of diphenyl carbonate in 15 ml of dimethylformamide. After further stirring for 30 minutes, the reaction mixture is poured into a mixture of 100 ml of ethyl acetate, 100 g of ice and 10 ml of hydrochloric acid. The organic phase is separated, washed with ice-water, dried over sodium sulfate and concentrated by evaporation. Recrystallisation from ether/Petroleum ether (1:1) yields 2.8 g of N-[2-(3,3,3-trifluoropropyl)-phenyl]-phenylcarbamate, m.p. 116°-119° C.

(b)
N-[2-(3,3,3-Trifluoropropyl)-phenylsulfonyl]-N'-(4-dimethylamino-6-methoxy-pyrimidin-2-yl)-urea A mixture of 2.65 g of N-[2-(3,3,3-trifluoropropyl)-phenyl]-phenylcarbamate and 1.18 g of 2-amino-4-dimethylamino-6-methoxy-pyrimidine in 20 ml of absolute dioxane is refluxed for 90 minutes; it is afterwards cooled to 20° C. and concentrated by evaporation. The yield after recrystallisation from a mixture of acetone and ether is 1.65 g of N-[2-(3,3,3-trifluoropropyl)-phenylsulfonyl]-N'-(4-dimethylamino-6-methoxy-pyrimidin-2-yl)-urea, m.p. 183°-184° C.

Example H3

N-[2-(3,3,3-Trifluoropropyl)-phenylsulfonyl]-N'-(4-methoxy-6-methyl-1,3,5-triazin-2-yl)-urea 2.9 g of N-[2-(3,3,3-trifluoro-1-propenyl)-phenylsulfonyl]-N'-(4-methoxy-6-methyl-1,3,5-triazin-2-yl)-urea are dissolved in 50 ml of ethyl acetate; there are then added 1.5 g of a 5% palladium/charcoal catalyst, and the mixture is shaken for 16 hours at 20°-25° C. in a hydrogen atmosphere. The catalyst is filtered off, and the residue is completely concentrated by evaporation and subsequently crystallised from an acetone/ether mixture to thus obtain 2.2 g of N-[2-(3,3,3-trifluoropropyl)-phenylsulfonyl]-N'(4-methoxy-6-methyl-1,3,5-triazin-2-yl)-urea, m.p. 157°-158° C.

Example H4

N-(2-(3,3,3-Trifluoropropyl)-phenylsulfonyl]-N'-(4-methoxy-6-methylpyrimidin-2-yl)-urea A mixture of 2.53 g of 2-(3,3,3-trifluoropropyl)-phenylsulfonaamide, 2.59 g of 4-methoxy-6-methylpyrimidin-2-yl-phenylcarbamate, 1.52 g of 1,5-diazabicyclo(5.4.0)undece-5-ene and 20 ml of dioxane is stirred at 20°-25° C. room temperature for 3 hours. The mixture is subsequently poured into water, acidified with 10% hydrochloric acid and extracted with ethyl acetate; the organic phase is then dried over sodium sulfate, and the residue is completely concentrated by evaporation and recrystallised from an acetone/ether mixture (1:5) to obtain 3.5 g of N-[2-(3,3,3-trifluoropropyl)-phenylsulfonyl]-N'-(4-methoxy-6-methyl-pyrimidin-2-yl)-urea, m.p. 174°-175° C.

The intermediates and final products listed in the following Tables are produced in an analogous manner.

TABLE 1

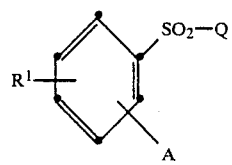

| No. | A | Position of A | R¹ | Q | Physical data |
|---|---|---|---|---|---|
| 1.1 | —CH$_2$—CH$_2$—CF$_3$ | 2 | H | Cl | |

TABLE 1-continued

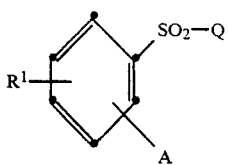

| No. | A | Position of A | R¹ | Q | Physical data |
|---|---|---|---|---|---|
| 1.2 | —CH₂—CH₂—CF₃ | 2 | H | NH₂ | m.p. 148–149° C. |
| 1.3 | —CH₂—CH₂—CF₃ | 2 | H | —N=C=O | oil |
| 1.4 | —CH₂—CH₂—CF₃ | 2 | H | —NH—CO—OC₆H₅ | m.p. 116–119° C. |
| 1.5 | —CH₂—CH₂—CF₂—CH₃ | 2 | H | Cl | |
| 1.6 | —CH₂—CH₂—CF₂—CH₃ | 2 | H | NH₂ | |
| 1.7 | —CH₂—CH₂—CF₂—CH₃ | 2 | H | —N=C=O | |
| 1.8 | —CH₂—CH₂—CF₂—CH₃ | 2 | H | —NH—CO—O₅C₆H₅ | |

TABLE 2

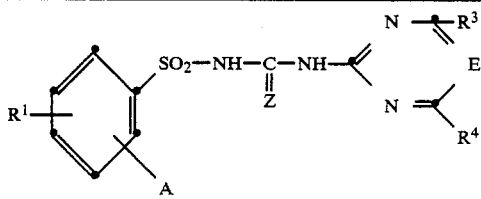

| No. | A | Position of A | R¹ | R³ | R⁴ | E | Z | m.p. [°C.] |
|---|---|---|---|---|---|---|---|---|
| 2.1 | —CH₂—CH₂—CF₃ | 2 | H | CH₃ | OCH₃ | N | O | 157–158 |
| 2.2 | —CH₂—CH₂—CF₃ | 2 | H | OCH₃ | OCH₃ | N | O | 177–178 |
| 2.3 | —CH₂—CH₂—CF₃ | 2 | H | CH₃ | OC₂H₅ | N | O | 145–146 |
| 2.4 | —CH₂—CH₂—CF₃ | 2 | H | C₂H₅ | OCH₃ | N | O | |
| 2.5 | —CH₂—CH₂—CF₃ | 2 | H | C₂H₅ | OC₂H₅ | N | O | |
| 2.6 | —CH₂—CH₂—CF₃ | 2 | H | OCH₃ | —OCH₂—CF₃ | N | O | |
| 2.7 | —CH₂—CH₂—CF₃ | 2 | H | CH₃ | —OCH₂—CF₃ | N | O | |
| 2.8 | —CH₂—CH₂—CF₃ | 2 | H | OCH₃ | —N(CH₃)₂ | N | O | |
| 2.9 | —CH₂—CH₂—CF₃ | 2 | H | OCH₃ | OC₃H₇-i | N | O | |
| 2.10 | —CH₂—CH₂—CF₃ | 2 | H | SCH₃ | OCH₃ | N | O | |
| 2.11 | —CH₂—CH₂—CF₃ | 2 | H | OCH₃ | —NHCH₃ | N | O | |
| 2.12 | —CH₂—CH₂—CF₃ | 2 | H | CH₃ | CH₃ | N | O | |
| 2.13 | —CH₂—CH₂—CF₃ | 2 | H | SCHF₂ | OCH₃ | N | O | |
| 2.14 | —CH₂—CH₂—CF₂—CH₃ | 2 | H | CH₃ | OCH₃ | N | O | 150–152 |
| 2.15 | —CH₂—CH₂—CF₂—CH₃ | 2 | H | OCH₃ | OCH₃ | N | O | |
| 2.16 | —CH₂—CH₂—CF₂—CH₃ | 2 | H | CH₃ | OC₂H₅ | N | O | |
| 2.17 | —CH₂—CH₂—CF₂—CH₃ | 2 | H | C₂H₅ | OCH₃ | N | O | |
| 2.18 | —CH₂—CH₂·CF₂—CH₃ | 2 | H | OCH₃ | —N(CH₃)₂ | N | O | |
| 2.19 | —CH₂—CH₂—CF₂—CH₃ | 2 | H | OCH₃ | —NHCH₃ | N | O | |
| 2.20 | —CH₂—CH₂—CF₂—CH₃ | 2 | H | OCH₃ | —OCH₂—CF₃ | N | O | |
| 2.21 | —CH₂—CH₂—CF₃ | 3 | H | CH₃ | OCH₃ | N | O | |
| 2.22 | —CH₂—CH₂—CF₃ | 3 | H | OCH₃ | OCH₃ | N | O | |
| 2.23 | —CH₂—CH₂—CF₃ | 3 | H | CH₃ | OC₂H₅ | N | O | |
| 2.24 | —CH₂—CH₂—CF₃ | 3 | H | C₂H₅ | OCH₃ | N | O | |
| 2.25 | —CH₂—CH₂—CF₃ | 3 | H | OCH₃ | —N(CH₃)₂ | N | O | |
| 2.26 | —CH₂—CH₂—CF₃ | 3 | H | OCH₃ | —NHCH₃ | N | O | |
| 2.27 | —CH₂—CH₂—CF₃ | 3 | H | OCH₃ | —OCH₂—CF₃ | N | O | |
| 2.28 | —CH₂—CH₂—CF₃ | 2 | H | CH₃ | CH₃ | CH | O | |
| 2.29 | —CH₂—CH₂—CF₃ | 2 | H | CH₃ | OCH₃ | CH | O | 174–175 |
| 2.30 | —CH₂—CH₂—CF₃ | 2 | H | CH₃ | —OCH₂—CF₃ | CH | O | |
| 2.31 | —CH₂—CH₂—CF₃ | 2 | H | CH₃ | OC₂H₅ | CH | O | |
| 2.32 | —CH₂—CH₂—CF₃ | 2 | H | OCH₃ | Cl | CH | O | 191–192 |
| 2.33 | —CH₂—CH₂—CF₃ | 2 | H | OCH₃ | OCH₃ | CH | O | 182–183 |
| 2.34 | —CH₂—CH₂—CF₃ | 2 | H | OCH₃ | SCHF₂ | CH | O | |
| 2.35 | —CH₂—CH₂—CF₃ | 2 | H | OCH₃ | —N(CH₃)₂ | CH | O | 183–184 |
| 2.36 | —CH₂—CH₂—CF₃ | 2 | H | OCH₃ | —NHCH₃ | CH | O | |
| 2.37 | —CH₂—CH₂—CF₃ | 2 | H | OCH₃ | CH₂F | CH | O | |
| 2.38 | —CH₂—CH₂—CF₃ | 2 | H | OCH₃ | —CF₃ | CH | O | |
| 2.39 | —CH₂—CH₂—CF₃ | 2 | H | OCH₃ | SCH₃ | CH | O | |
| 2.40 | —CH₂—CH₂—CF₃ | 2 | H | OCH₃ | —OCH₂—CF₃ | CH | O | |
| 2.41 | —CH₂—CH₂—CF₃ | 2 | H | OCH₃ | —CH₂—OCH₃ | CH | O | |
| 2.42 | —CH₂—CH₂—CF₃ | 2 | H | OCH₃ | —CH₂—OC₂H₅ | CH | O | |
| 2.43 | —CH₂—CH₂—CF₂—CH₃ | 2 | H | CH₃ | OCH₃ | CH | O | |
| 2.44 | —CH₂—CH₂—CF₂—CH₃ | 2 | H | CH₃ | OCH₃ | CH | O | |
| 2.45 | —CH₂—CH₂—CF₂—CH₃ | 2 | H | OCH₃ | Cl | CH | O | |
| 2.46 | —CH₂—CH₂—CF₂—CH₃ | 2 | H | OCH₃ | —N(CH₃)₂ | CH | O | |
| 2.47 | —CH₂—CH₂—CF₂—CH₃ | 2 | H | OCH₃ | CH₂F | CH | O | |

TABLE 2-continued

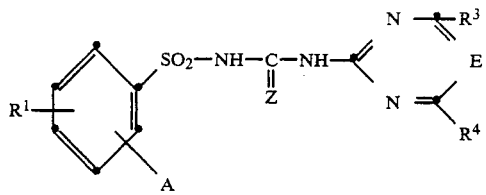

| No. | A | Position of A | R¹ | R³ | R⁴ | E | Z | m.p. [°C.] |
|---|---|---|---|---|---|---|---|---|
| 2.48 | $-CH_2-CH_2-CF_2-CH_3$ | 2 | H | $OCH_3$ | $CH_2F$ | CH | O | |
| 2.49 | $-CH_2-CH_2-CF_2-CH_3$ | 2 | H | $OCH_3$ | $-CH_2-OCH_3$ | CH | O | |
| 2.50 | $-CH_2-CH_2-CF_2-CH_3$ | 2 | H | $OCH_3$ | $OCH_3$ | CH | O | |
| 2.51 | $-CH_2-CH_2-CF_3$ | 3 | H | $OCH_3$ | $CH_3$ | CH | O | |
| 2.52 | $-CH_2-CH_2-CF_3$ | 3 | H | $CH_3$ | $CH_3$ | CH | O | |
| 2.53 | $-CH_2-CH_2-CF_3$ | 3 | H | $OCH_3$ | Cl | CH | O | |
| 2.54 | $-CH_2-CH_2-CF_3$ | 3 | H | $OCH_3$ | $-N(CH_3)_2$ | CH | O | |
| 2.55 | $-CH_2-CH_2-CF_3$ | 3 | H | $OCH_3$ | $CH_2F$ | CH | O | |
| 2.56 | $-CH_2-CH_2-CF_3$ | 3 | H | $OCH_3$ | $-CH_2-OCH_3$ | CH | O | |
| 2.57 | $-CH_2-CH_2-CF_3$ | 3 | H | $OCH_3$ | $OCH_3$ | CH | O | |

Formulation Examples

Example F1

Formulation Examples for active ingredients of the formula I (%=percent by weight)

| (a) Wettable powder | (a) | (b) | (c) |
|---|---|---|---|
| active ingredient | 20% | 60% | 0.5% |
| sodium lignin sulfonate | 5% | 5% | 5% |
| sodium lauryl sulfate | 3% | — | — |
| sodium diisobutylnaphthalene sulfonate | — | 6% | 6% |
| octylphenolpolyethylene glycol ether (7–8 mols of ethylene oxide) | — | 2% | 2% |
| highly dispersed silicic acid | 5% | 27% | 27% |
| kaolin | 67% | — | — |
| sodium chloride | — | — | 59.5% |

The active ingredient is well mixed with the additives and ground in a suitable mill. There are obtained wettable powders which can be diluted with water to give suspensions of the concentration desired.

| (b) Emulsion concentrate | (a) | (b) |
|---|---|---|
| active ingredient | 10% | 1% |
| octylphenolpolyethylene glycol ether (4–5 mols of ethylene oxide) | 3% | 3% |
| calcium dodecyl benzene sulfonate | 3% | 3% |
| castor oil polyglycol ether (36 mols of ethylene oxide) | 4% | 4% |
| cyclohexanone | 30% | 10% |
| xylene mixture | 50% | 79% |

Emulsions of the concentration desired can be obtained from this concentrate by dilution with water.

| (c) Dust | (a) | (b) |
|---|---|---|
| active ingredient | 0.1% | 1% |
| talcum | 99.9% | — |
| kaolin | — | 99% |

Dusts ready for use are obtained by mixing the active-ingredient with the carriers, and grinding the mixture in a suitable mill.

| (d) Extruder granulate | (a) | (b) |
|---|---|---|
| active ingredient | 10% | 1% |
| sodium lignin sulfonate | 2% | 2% |
| carboxymethylcellulose | 1% | 1% |
| kaolin | 87% | 96% |

The active ingredient is mixed with the additives, and the mixture is then ground and moistened with water. It is extruded and subsequently dried in a stream of air.

(e) Coated granulate

| (e) Coated granulate | |
|---|---|
| active ingredient | 3% |
| polyethylene glycol (MW 200) | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| active ingredient | 40% | 5% |
| ethylene glycol | 10% | 10% |
| nonylphenolpolyethylene glycol ether (15 mols of ethylene oxide) | 6% | 1% |
| sodium lignin sulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the additives. There is thus obtained a suspension concentrate from which can be produced, by dilution with water, suspensions of the concentration desired.

| (g) Salt solution | |
|---|---|
| active ingredient | 5% |
| isopropylamine | 1% |
| octylphenolpolyethylene glycol ether (78 mols of ethylene oxide) | 3% |

| (g) Salt solution | |
|---|---|
| water | 91% |

Biological Examples

Example B1: Herbicidal action before emergence of the plants

Plastics pots are filled with expanded vermiculite (density: 0.135 g/cm$^3$, water-absorption capacity: 0.565 l/l). After saturation of the non-adsorptive vermiculite with an aqueous active-ingredient emulsion in deionised water, which contains the active ingredient at a concentration of 70.8 ppm, seeds of the following plants are sown on the surface: *Nasturtium officinalis, Agrostis tenuis, Stellaria media* and *Digitaria sanguinalis*. The test vessels are subsequently kept in a climatic chamber at 20° C., with an illumination of about 20 k lux and a relative humidity of 70%. During the germination phase of 4 to 5 days, the pots are covered over with light-permeable material in order to raise the local air humidity and watered with deionised water. After the 5th day, 0.5% of a commercial liquid fertiliser (®Greenzit, ex Ciba-Geigy) is added to the water. The test is evaluated 12 days after sowing, and the effects on the test plants assessed according to the following scale of ratings:

1 plants have not germinated or are totally destroyed
2-3 very strong action
4-6 medium action
7-8 weak action
9 no action (as untreated control plants).

Pre-emergence action

Concentration of the active-ingredient emulsion: 70.8 ppm

| Active ingredient No. | Test plant | | | |
|---|---|---|---|---|
| | Nasturtium | Stellaria | Agrostis | Digitaria |
| 2.1 | 2 | 2 | 2 | 7 |
| 2.2 | 2 | 6 | 3 | 7 |
| 2.3 | 2 | 2 | 3 | 4 |
| 2.14 | 3 | 2 | 3 | 4 |
| 2.29 | 1 | 2 | 1 | 2 |
| 2.32 | 1 | 3 | 1 | 5 |
| 2.33 | 1 | 2 | 1 | 3 |
| 2.35 | 1 | 1 | 1 | 1 |

Example B2

Verification of the Selective Herbicidal Action Before Emergence of the Plants

A number of plant seeds are sown in flower pots of 12-15 cm diameter in a greenhouse. Immediately afterwards, the surface of the soil is treated with an aqueous dispersion or solution of the active ingredient. The concentration applied correspond to amounts of active ingredient of 500, 125 and 30 g per hectare. The pots are then kept in the greenhouse at a temperature of 22°-25° C. with 50-70% relative humidity. The test is evaluated after 3 weeks, and the herbicidal action is assessed according to the scale of ratings given in Example B1.

| Action Applied amount g of AS/hectare | Compound No. 2.1 | | |
|---|---|---|---|
| Test plant | 500 | 125 | 30 |
| barley | 7 | 8 | 9 |
| wheat | 8 | 9 | 9 |
| maize | 6 | 7 | 9 |
| *Alopecurus myos.* | 2 | 4 | 5 |
| *Cyperus escul.* | 2 | 4 | 6 |
| Abutilon | 1 | 2 | 3 |
| *Sida spinosa* | 2 | 2 | 3 |
| Xanthium Sp. | 2 | 2 | 2 |
| *Amaranthus ret.* | 1 | 2 | 2 |
| Chenopodium Sp. | 2 | 2 | 3 |
| *Solanum nigrum* | 3 | 3 | 3 |
| Ipomoea | 2 | 2 | 2 |
| Sinapis | 2 | 2 | 2 |
| Stellaria | 2 | 2 | 2 |
| *Chrysanthe.leuc.* | 2 | 2 | 2 |
| Viola tricolor | 2 | 2 | 2 |
| Veronica Sp. | 1 | 1 | 2 |

EXAMPLE B3

Reduction in Growth of Tropical Leguminous Cover Crops

The test plants (*Centrosema plumieri* and *Centrosema pubescens*) are cultivated to the fully grown stage, and then cut back to a height of 60 cm. After 7 days, the active ingredient is sprayed on in the form of an aqueous emulsion. The test plants are maintained at 70% relative humidity and with 6000 lux of artificial light, 14 hours per day, at temperatures of 27° C. by day and 21° C. by night. The test results are assessed 4 weeks after application of the emulsion. The new growth occurring compared with that on the control plants is estimated and weighed, and the phytotoxicity is evaluated. The plants treated with the active ingredients of the formula I show in this test a clear reduction in new growth (less than 20% of the new growth occurring on untreated control plants), without the test plants having suffered damage.

Example B4

Regulation of growth of soya-bean plants

Soya-beans of the "Hark" variety are sown in plastic containers holding a soil/peat/sand mixture in the ratio of 6:3:1, and are placed into a climatic chamber. By optimum choice of temperature, illumination, fertiliser addition and watering, the plants develop over about 5 weeks into the 5-6 trifoliate stage. At this point, the plants are sprayed until thoroughly dripping wet with the aqueous liquor of an active ingredient of the formula I, the active-ingredient concentration being equivalent to up to 100 g of active ingredient per hectare. An assessment of the results is made about 5 weeks after application of the active ingredient. The active ingredients of the formula I according to the invention produce a marked increase in the number and in the weight of the pods on the leading shoots compared with the number and weight of pods on the untreated control plants.

Example B5

Reduction in growth of cereals

The cereal varieties *Hordeum vulgare* (spring barley) and Secale (spring rye) are sown in plastics pots containing sterilised soil in a greenhouse, and watered as required. The young shoots are sprayed, about 21 days after sowing, with the aqueous spray liquor of an active ingredient of the formula I. The amount applied is equivalent to up to 100 g of active ingredient per hectare, and 21 days after application, the growth of the cereals is assessed. The treated plants show a reduction in the extent of new growth compared with that on the untreated control plants (60–90% of the new growth on the control plants), and also in part an increase in the diameter of the stems of the plants.

Example B6

Reduction of Growth of Grasses

The grasses *Lolium perenne, Poa pratensis, Festuca ovina, Dactylis glomerata* and *Cynodon dactylon* are sown, in a greenhouse, in plastics dishes containing a soil/peat/sand mixture (6:3:1), and watered as required. The emerged grasses are cut back weekly to a height of 4 cm, and are sprayed, about 50 days after sowing and one day after the final cutting, with the aqueous spray liquor of an active ingredient of the formula I. The amount of active ingredient corresponds, when converted, to up to 100 g per hectare. The growth of the grasses is assessed 21 days after application.

The compounds of the formula I effect a reduction of new growth of around 10–30%, compared with the new growth of the untreated control grasses.

What is claimed is:

1. A phenylsulfonylisocyanate or -isothiocyanate of the formula IV

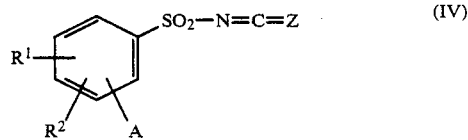

wherein
A is 3,3,3-trifluoropropyl or 3,3-difluorobutyl,
$R^1$ is hydrogen, halogen, nitro, cyano, $C_1$–$C_4$-alkyl, $C_1$–$C_4$-haloalkyl, $C_1$–$C_4$-alkoxy, $C_1$–$C_4$-alkylthio, $C_1$–$C_4$-alkylsulfinyl, $C_1$–$C_4$-alkylsulfonyl, —CO—$R^6$, —$NR^7R^8$, —CO—$NR^9R^{10}$ or —$SO_2$—$NR^{11}R^{12}$,
$R^2$ is hydrogen, halogen, $C_1$–$C_4$-alkyl, $C_1$–$C_4$-alkoxy, $C_1$–$C_4$alkylthio, $C_1$–$C_4$-alkylsulfinyl or $C_1$–$C_4$-alkylsulfonyl,
$R^6$ is $C_1$–$C_4$-alkoxy, $C_1$–$C_4$-haloalkoxy, $C_1$–$C_4$-alkylthio, $C_2$–$C_6$-alkoxyalkoxy, hydrogen, $C_1$–$C_4$-alkyl or $C_1$–$C_4$-haloalkyl,
$R^7$, $R^8$, $R^9$, $R^{10}$, $R^{11}$ and $R^{12}$ independently of one another are each hydrogen or $C_1$–$C_4$-alkyl and
Z is oxygen or sulfur.
2. 2-(3,3,3,-Trifluoropropyl)phenylsulfonylisocyanate according to claim 1.

* * * * *